United States Patent [19]
Ohba et al.

[11] Patent Number: 5,683,704
[45] Date of Patent: Nov. 4, 1997

[54] COSMETIC COMPOSITION

[75] Inventors: Mihoko Ohba, Tokyo; Haruo Ogawa; Wataru Tokue, both of Kanagawa; Masahiro Matsuoka, Tokyo, all of Japan

[73] Assignee: Senju Pharmaceutical Co., Ltd., Osaka, Japan

[21] Appl. No.: 496,093

[22] Filed: Jun. 28, 1995

[30] Foreign Application Priority Data

Jun. 30, 1994 [JP] Japan ................................. 6-171888

[51] Int. Cl.$^6$ ................................. A61K 7/00; A61K 7/07
[52] U.S. Cl. .................. 424/401; 424/70.1; 424/70.11; 514/970; 514/972
[58] Field of Search ........................ 424/401, 70.1, 424/70.11; 514/970, 972

[56] References Cited

U.S. PATENT DOCUMENTS

| | | | |
|---|---|---|---|
| 4,966,779 | 10/1990 | Kirk | 426/72 |
| 5,053,222 | 10/1991 | Takasu et al. | 424/7 |
| 5,306,713 | 4/1994 | Suetsugu et al. | 514/100 |
| 5,364,631 | 11/1994 | Janoff et al. | 424/450 |

*Primary Examiner*—Sallie M. Gardner
*Attorney, Agent, or Firm*—Wenderoth, Lind & Ponack

[57] ABSTRACT

This invention is to provide a cosmetic composition which comprises dl-α-tocopheryl 2-L-ascorbyl phosphate phosphate and/or a salt thereof in stabilized condition. The cosmetic composition comprises one or more members of the group consisting of a polyhydric alcohol derivative, urea, and a sub-critical micelle concentration of a nonionic surfactant as formulated with said dl-α-tocopheryl 2-L-ascorbyl phosphate or salt thereof.

5 Claims, No Drawings

COSMETIC COMPOSITION

BACKGROUND OF THE INVENTION

1. Field of the Invention

The present invention relates to a cosmetic composition with a potent ameliorative effect on rough skin. More particularly, the invention is concerned with enhancement of the stability of dl-α-tocopheryl 2-L-ascorbyl phosphate or a salt thereof as included in a cosmetic formulation for antioxidant and humectant effects.

2. Description of the Prior Art

Cosmetic preparations, particularly those designed to have an ameliorative effect on rough skin, are sometimes supplemented with dl-α-tocopheryl 2-L-ascorbyl phosphate and/or a salt thereof for improved oxidation resistance and moisture retention. However, because of its inherent chemical instability, dl-α-tocopheryl 2-L-ascorbyl phosphate or its salt so included in a cosmetic formulation undergoes decomposition or aging with the passage of time or on prolonged exposure to solar or other radiation so that the cosmetic product tends to be degraded and develops a discoloration problem.

In view of the above state of the art, the inventors of the present invention did a great deal of research to develop stable cosmetic preparations through inhibition of the decomposition reaction of dl-α-tocopheryl 2-L-ascorbyl phosphate or its salt. The research has culminated in the perfection of the present invention.

The object of the present invention is to provide a cosmetic composition containing dl-α-tocopheryl 2-L-ascorbyl phosphate or a salt thereof in stabilized condition.

After a series of intensive investigations, the inventors of the present invention discovered that when one or more members of the group consisting of a polyhydric alcohol derivative, urea, and a sub-critical micelle concentration of a nonionic surfactant are formulated with either dl-α-tocopheryl 2-L-ascorbyl phosphate or a salt thereof, or both, in a cosmetic composition, the micelle formation of the dl-α-tocopheryl 2-L-ascorbyl phosphate and/or salt thereof is inhibited so that the temperature-dependent decomposition of the dl-α-tocopheryl 2-L-ascorbyl diester and/or salt thereof can be prevented. The present invention is based on the above finding.

SUMMARY OF THE INVENTION

The present invention is, therefore, concerned with a cosmetic composition comprising one or more members of the group consisting of a polyhydric alcohol derivative, urea, and a sub-critical micelle concentration of a nonionic surfactant as formulated with dl-α-tocopheryl 2-L-ascorbyl phosphate and/or a salt thereof.

DETAILED DESCRIPTION OF THE INVENTION

The present invention is now described in detail. It appears to be the formation of micelles that causes instability of dl-α-tocopheryl 2-L-ascorbyl phosphate or its salt in a cosmetic preparation. In the present invention, this micelle formation of dl-α-tocopheryl 2-L-ascorbyl phosphate or a salt thereof is prevented by including an inhibitor of said micelle formation in the formulation to thereby stabilize the cosmetic preparation.

The micelle formation inhibitor for use in accordance with the present invention is a polyhydric alcohol derivative, urea, and/or a sub-critical micelle concentration of a nonionic surfactant.

The polyhydric alcohol derivative mentioned above includes but is not limited to the ethers of polyoxypropylene (POP) or polyoxyethylene (POE) with polyhydric alcohols. Among the polyhydric alcohols are glycerol, polyglycerol, sorbitol and methyl glucoside, to mention just a few. The particularly preferred polyhydric alcohol derivatives are polyoxypropylene diglyceryl ether, polyoxypropylene methyl glucoside and polyoxyethylene methyl glucoside.

The nonionic surfactant preferably has an HLB number of 10 or 20. The preferred types of nonionic surfactants are polyoxy(lower)alkylene esters such as polyoxyethylene higher fatty acid esters; polyoxy(lower)alkylene ethers such as higher aliphatic alcohol polyoxyethylene ethers; and ether-ester type nonionic surfactants such as the compound formed as some of the hydroxyl groups of a polyhydric alcohol or a dehydration product thereof, e.g. sorbitol or sorbitan, form ether bonds with polyoxyethylene, with the other hydroxyl groups forming ester bonds with a higher fatty acid and polyoxyethylene derivatives of castor oil. Particularly preferred are polyoxyethylene hydrogenated castor oil (5–100 mols), polyoxyethylene octyldodecyl ether (10–30 mols) and polyoxyethylene monoglyceryl isostearate (10–100 mols).

These substances can be used independently or in combination.

The formulating amount of said polyhydric alcohol derivative is 0.1–30 weight %, preferably 1–15 weight %, and for still better results, 5–15 weight %. If it is less than 0.1 weight %, the stability of dl-α-tocopheryl 2-L-ascorbyl phosphate and its salt will not be sufficiently sustained. On the other hand, if the amount exceeds 30 weight %, no further increase in the effect will be obtained.

The formulating amount of urea is 1–20 weight %, preferably 5–20 weight %, and for still better results, 5–10 weight %. If it is less than 1 weight %, dl-α-tocopheryl 2-L-ascorbyl phosphate will not be sufficiently stable. On the other hand, if 20 weight % is exceeded, no further increase in the effect will be obtained.

The formulating amount of said nonionic surfactant should be less than the critical micelle concentration, that is to say the critical concentration for micelle formation. Though this critical concentration is different with types of surfactants, it may for example be 0.01 weight %.

The salt of dl-α-tocopheryl 2-L-ascorbyl phosphate is preferably an alkali metal salt, e.g. sodium salt or potassium salt, or an alkaline earth metal salt, e.g. calcium salt or magnesium salt. The preferred formulating amount of dl-α-tocopheryl 2-L-ascorbyl phosphate or its salt is 0.01–1 weight %. If it is less than 0.01 weight %, the effect of dl-α-tocopheryl 2-L-ascorbyl phosphate or its salt will not be expressed. On the other hand, if 1 weight % is exceeded, no further increase in the effect will be obtained.

In the practice of the present invention, where necessary and unless the effect of the invention is adversely affected, various oils and fats, hydrocarbons, fatty acids, water-soluble polymers, particles, ultraviolet absorbers, preservatives, pharmacologically active substances, colors, perfumes, and other ingredients in common usage in the cosmetic industry can also be incorporated.

EXAMPLES

The following examples are intended to describe the present invention in further detail and should by no means be construed as defining the scope of the invention. In the following examples, all the formulating amounts of various ingredients are expressed in weight %.

Examples 1-5

Using polyoxypropylene diglyceryl ether as the polyhydric alcohol derivative in the varying proportions indicated in Table 1, cosmetic compositions were prepared otherwise in accordance with the following formulation.

dl-α-Tocopheryl 2-L-ascorbyl
phosphate potassium 0.05
Phenoxyethanol 0.3
Citric acid 0.01
Sodium citrate 0.09
Polyoxypropylene diglyceryl      a varying
ether                            concentration
Water                            balance A storage test was performed using each of the compositions thus obtained. Thus, a 50 ml gas-tight glass container was filled with each composition substantially up to capacity and kept stored at 50° C. for 1 or 2 months. In parallel, the compositions were respectively stored at 0° C. for 2 months to generate control data. The results, with the initial amount of dl-α-tocopheryl 2-L-ascorbyl phosphate potassium being taken as 100, are shown in Table 1.

shown in Table 2. In Examples 6–12, polyoxypropylene diglyceryl ether (9 mols) was used as the polyhydric alcohol derivative and polyoxyethylene hydrogenated castor oil (60 mols) as the nonionic surfactant of sub-critical micelle concentration. Comparative Example 2 represents the composition available on elimination of polyoxypropylene diglyceryl ether (9 mols) and polyoxyethylene-hydrogenated castor oil (60 mols) from Examples 6–12. For production, the respective ingredients were dissolved in purified water.

The cosmetic compositions of the above Examples and Comparative Example were stored at 50° C. for 2 months and the percentage residues of dl-α-tocopheryl 2-L-ascorbyl phosphate potassium were determined. It is assumed that the higher the % residue value of the dl-α-tocopheryl 2-L-ascorbyl phosphate potassium, the higher is its stability. The percentage residue values of dl-α-tocopheryl 2-L-ascorbyl phosphate potassium were calculated by the following equation.

$$\text{Percentage residue (\%)} = \frac{\text{Amount after 2 months at 50° C.}}{\text{Amount after 2 months at 0° C.}}$$

The percentage residue values for the cosmetic compositions of Examples 6–12 after 2 months at 50° C. were invariably as high as more than 90%, indicating that dl-α-tocopheryl 2-L-ascorbyl potassium remained very stable. On the other hand, the percentage residue value for Comparative Example 2 decreased to the order of 70%, indicating that dl-α-tocopheryl 2-L-ascorbyl phosphate potassium was rather unstable.

TABLE 1

|  |  | Comparative Example 1 | Example 1 | Example 2 | Example 3 | Example 4 | Example 5 |
|---|---|---|---|---|---|---|---|
| Concentration of polyoxypropylene diglyceryl ether (wt. %) | | 0 | 1 | 3 | 5 | 7 | 10 |
| Amount of dl-α-tocopheryl 2-L-ascorbyl phosphate potassium | After 2 months at 0° C. | 100.24 | 101.37 | 100.77 | 101.90 | 102.08 | 101.44 |
| | After 1 month at 50° C. | 88.16 | 92.98 | 92.87 | 95.16 | 94.75 | 94.76 |
| | After 2 months at 50° C. | 79.22 | 86.04 | 87.07 | 89.56 | 88.38 | 92.96 |

Examples 6–12, Comparative Example 2

Cosmetic compositions of Examples 6–12 and Comparative Example 2 were prepared according to the formulations

TABLE 2

| Ingredient | Example 6 | Example 7 | Example 8 | Example 9 | Example 10 | Example 11 | Example 12 | Comparative Example 2 |
|---|---|---|---|---|---|---|---|---|
| Purified water | 94.38 | 89.39 | 84.39 | 79.39 | 84.38 | 89.38 | 79.38 | 94.39 |
| dl-α-Tocopheryl 2-L-ascorbyl phosphate K salt | 0.2 | 0.2 | 0.2 | 0.2 | 0.2 | 0.2 | 0.2 | 0.2 |
| Glycerin | 5 | 5 | 5 | 5 | 5 | 5 | 5 | 5 |
| Phenoxyethanol | 0.2 | 0.2 | 0.2 | 0.2 | 0.2 | 0.2 | 0.2 | 0.2 |
| Methyl p-hydroxybenzoate | 0.1 | 0.1 | 0.1 | 0.1 | 0.1 | 0.1 | 0.1 | 0.1 |
| Citric acid | 0.01 | 0.01 | 0.01 | 0.01 | 0.01 | 0.01 | 0.01 | 0.01 |
| Sodium citrate | 0.1 | 0.1 | 0.1 | 0.1 | 0.1 | 0.1 | 0.1 | 0.1 |
| Urea | — | — | 10 | 10 | 10 | — | 10 | — |
| Polyoxypropylene diglycidyl ether (9M) | — | 5 | — | 5 | — | 5 | 5 | — |

TABLE 2-continued

| Ingredient | Example 6 | Example 7 | Example 8 | Example 9 | Example 10 | Example 11 | Example 12 | Comparative Example 2 |
|---|---|---|---|---|---|---|---|---|
| Polyoxyethylene hydrogenated castor oil (60M) | 0.01 | — | — | — | 0.01 | 0.01 | 0.01 | — |
| Total | 100.0 | 100.0 | 100.0 | 100.0 | 100.0 | 100.0 | 100.0 | 100.0 |
| % Residue of dl-α-tocopheryl 2-L-ascorbyl phosphate K salt after 2 months at 50° C. | 92.8 | 93.4 | 90.1 | 96.4 | 96.3 | 98.1 | 99.8 | 79.2 |

Examples 13 (Moisturizing Cream)

A moisturizing cream was prepared according to the following formula.

(A) Cetanol 2.0
Beeswax 1.0
Solid paraffin 1.0
Stearic acid 2.0
Petrolatum 5.0
Liquid paraffin 5.0
Squalane 2.0
Pentaerythritol tetraoctanoate 3.5
POE(20) sorbitan stearate 1.6
Diglycerin distearate 1.4
Propyl p-hydroxybenzoate 0.3
Vitamin E 0.1
Perfume 0.2
(B) POP(10) alkyl glucoside 20.0
Glycerol 5.0
Dipropylene glycol 5.0
Sodium hyaluronate 0.1
dl-α-tocopheryl 2-L-ascorbyl phosphate potassium 0.8
Potassium hydroxide 0.08
Purified water balance
(Process)

The oil phase (A) and the water phase (B) were independently melted and dissolved by heating under agitation. The oil phase was added to the water phase and the resulting emulsion was cooled to provide a moisturizing cream.

Example 14 (Moisturizing Emulsion)

A moisturizing emulsion was prepared according to the following formula.

(A) Beeswax 1.0
Petrolatum 2.0
Deodorized lanolin 1.5
Jojoba oil 3.0
Cetyl isooctanoate 4.0
Glyceryl trioctanoate 5.0
POE(2) octyldodecanol 2.0
Primrose oil 0.5
Ethyl p-hydroxybenzoate 0.2
Butyl p-hydroxybenzoate 0.1
2-Ethylhexyl p-methoxycinnamate 0.5
Perfume 0.2
(B) POP(9) diglyceryl ether 7.0
1,3-Butylene glycol 6.0
Carboxyvinyl polymer 0.2
Potassium hydroxide 0.07
Monoammonium glycyrrhetinate 0.1
dl-α-Tocopheryl 2-L-ascorbyl phosphate potassium 0.5
Purified water balance
(Process)

The procedure of Example 13 was followed to provide a moisturizing emulsion.

Example 15 (Toilet Water)

A toilet water was prepared according to the following formula.

(A) Glycerol 8.0
Sorbitol 6.0
Sodium methacrylate 0.1
dl-α-Tocopheryl 2-L-ascorbyl phosphate potassium 0.05
Citric acid 0.04
Sodium citrate 0.16
(B) Ethanol 10.0
POP(60)-hydrogenated castor oil 0.01
Purified lecithin 0.04
Methyl p-hydroxybenzoate 0.1
(Process)

The water phase (A) and the alcohol phase (B) were respectively melted well and the alcohol phase was added to the water phase to provide a toilet water.

Example 16 (Hand Cream)

A hand cream was prepared according to the following formula.

(A) Liquid paraffin 5.0
Petrolatum 5.0
Stearyl alcohol 2.0
Olive oil 2.0
Methylphenylpolysiloxane 1.0
Stearic acid 1.5
Behenic acid 1.5
POE(50)-hydrogenated castor oil 0.5
POE(10)-glyceryl monostearate 2.0
Butyl p-hydroxybenzoate 0.2

Perfume 0.05
(B) Glycerin 10.0
1,3-Butylene glycol 6.0
Dipropylene glycol 3.0
Sodium hyaluronate 0.1
Edetic acid salt 0.05
Dipotassium glycyrrhetinate 0.1
dl-α-Tocopheryl 2-L-ascorbyl
phosphate potassium 0.4
Urea 13.0
Sodium hydroxymethoxy-
benzophenonesulfonate 0.1
Purified water Balance
(Process)

The procedure of Example 13 was repeated to provide a hand cream.

As described above, the cosmetic composition of the present invention is a composition containing dl-α-tocopheryl 2-L-ascorbyl phosphate and/or a salt thereof in stable condition and, as such, exerting an ameliorative effect on rough skin, which cosmetic composition comprises one or more members of the group consisting of a polyhydric alcohol derivative, urea, and a sub-critical micelle concentration of a nonionic surfactants as formulated with said dl-α-tocopheryl 2-L-ascorbyl phosphate or salt thereof.

What is claimed is:

1. A method of stabilizing dl-α-tocopheryl 2-L-ascorbyl phosphate and/or a salt thereof against decomposition in a cosmetic composition by incorporating in said composition a stabilizing effective amount of one or more members of the group consisting of polyoxypropylene diglyceryl ether, polyoxypropylene methyl glucoside, polyoxyethylene methyl glucoside, urea, and a concentration below the concentration critical for micelle formation of at least one member of the group consisting of polyoxyethylene hydrogenated castor oil, polyoxyethylene octyldodecyl ether and polyoxyethylene monoglyceryl isostearate.

2. A method according to claim 1 wherein at least one member selected from the group consisting of polyoxypropylene diglyceryl ether, polyoxypropylene methyl glucoside, and polyoxyethylene methyl glucoside is employed.

3. A method according to claim 2 wherein said member is employed in a proportion of 0.1–30 weight %.

4. A method according to claim 1 wherein urea is employed in a proportion of 1–20 weight %.

5. A method according to claim 1 wherein at least one member of the group consisting of polyoxyethylene hydrogenated castor oil, polyoxyethylene octyldodecyl ether and polyoxyethylene monoglyceryl isostearate is employed in a proportion of not more than 0.01 weight %.

* * * * *